United States Patent [19]

Suga et al.

[11] Patent Number: 4,704,903
[45] Date of Patent: Nov. 10, 1987

[54] LIGHT FASTNESS/WEATHER RESISTANCE ACCELERATED TEST MACHINE WITH AN AIR MIXING REGULATOR

[75] Inventors: Shigeru Suga; Kiyoshi Chaki; Etsuji Natori; Shigeo Suga; Katsuaki Mitamura, all of Shinjuku, Japan

[73] Assignee: Suga Test Instruments Co., Ltd., Tokyo, Japan

[21] Appl. No.: 864,463

[22] Filed: May 19, 1986

[30] Foreign Application Priority Data

Jun. 19, 1985 [JP] Japan .................. 60-133286

[51] Int. Cl.$^4$ .................. G01N 17/00; G01N 25/00
[52] U.S. Cl. .................. 73/159; 73/865.6
[58] Field of Search .................. 73/865.6, 159; 374/57; 236/49

[56] References Cited

U.S. PATENT DOCUMENTS

| | | | |
|---|---|---|---|
| 2,167,472 | 7/1939 | Bedford | 236/49 |
| 2,935,261 | 5/1960 | Smith | 236/49 |
| 3,983,742 | 10/1976 | Suga | 73/865.6 |
| 4,526,318 | 7/1985 | Fleming et al. | 236/49 |

Primary Examiner—Stewart J. Levy
Assistant Examiner—Robert R. Raevis
Attorney, Agent, or Firm—Wenderoth, Lind & Ponack

[57] ABSTRACT

A light fastness/weather resistance accelerated test apparatus, including a test tank having a discharge duct, a light source at the center of the test tank with a sample rotating frame rotatable around the light source and a black panel thermometer mounted on the sample rotating frame. A sensor on the sample rotating frame senses the temperature at the position of a sample. An air flow regulator is provided on the test tank, a blower is mounted for discharging air into the bottom of the tank, and a circulating duct is connected between the air flow regulator and the blower. A damper in the air flow regulator is movable to open the inside of the tank to the discharge duct or to direct air from within the tank into the circulating duct. An air mixer has a further damper and a bypass opening into the air flow regulator. The further damper is controlled to direct air through the bypass in response to the temperature outside the apparatus.

6 Claims, 9 Drawing Figures

LIGHT FASTNESS/WEATHER RESISTANCE ACCELERATED TEST MACHINE WITH AN AIR MIXING REGULATOR

The present invention relates to a light fastness/weather resistance accelerated test machine for testing any type of material for light fastness or weather resistance.

BACKGROUND OF THE INVENTION AND PRIOR ART

Apparatus for carrying out accelerated tests for light fastness and weather resistance of materials is known. One such apparatus will be described with reference to FIG. 1. In FIG. 1 there is illustrated a sectional elevation view of a conventional accelerated light fastness/weather resistance testing machine having a test tank 1 which includes a light source 2 at the center thereof. A sample 4 is mounted on a sample rotating frame 3 rotatable about the light source 2 with the sample facing the light source, the sample 4 deteriorating during a test period in which it receives radiant heat emitted from the light source 2.

A temperature sensor 5 is fixed in the test tank 1 for measuring the dry-bulb temperature in the interior of the test tank 1, and a black panel thermometer 6 is mounted on the sample rotating frame 3 in juxtaposed relation to the sample 4, the indicated temperature being visually readable.

The temperature sensor 5 is used for controlling an air temperature regulator (not shown) and is located in an air outlet, the temperature sensor 5 serving to set the air temperature regulator so that the black panel temperature is held at a constant value.

Alternatively, in place of the air temperature regulator, there has been used a means for mounting a black panel temperature regulator 7 on the sample rotating frame. This is called a black panel temperature control system.

The temperature of the sample surface is raised due to the increase of the air temperature in the tank and radiant heat emitted from the light source 2, and a control signal is taken out from the temperature sensor 5 for the air temperature regulator or the black panel temperature regulator 7 to make temperature control possible, so that the temperature of the sample surface can be held constant.

The black panel thermometer 6 comprises a bimetal type dial thermometer, the barrel of which is mounted on a stainless plate, with black paint applied thereon.

An air flow regulator 8 is provided on the side of the test tank 1 and a blower 9 is provided at the base of the testing machine, the air regulator 8 and the blower 9 being interconnected by a circulation duct 10. A motor associated with the air regulator 8 is operated from the signal transmitted from the temperature sensor 5 through the air temperature regulator or the black panel temperature regulator 7 to thereby open and close a damper 11.

When the temperature in the tank becomes higher than the set temperature of the air temperature regulator or the black panel temperature regulator 7, the damper 11 is brought into a fully open state (FIG. 1 position) so that fresh air is introduced into the test tank 1 by means of the blower 9 through the air flow regulator 8 and the duct 10 and is then discharged through an exhaust duct 12.

When the tank temperature becomes lower than the set temperature, the damper 8 is fully closed (about 90° clockwise from the FIG. 1 position) so that no fresh air is introduced, but instead the air in the machine is caused to circulate within the tank through the circulation duct 10.

In this manner, according to the prior art apparatus, the tank temperature is regulated by switching the air flow path by switching the damper 8 between a fully open state and a fully closed state.

Such prior art testing apparatus is shown in Japanese Industrial Standard B7751-1974, "Ultraviolet Ray Carbon Arc Lamp Type Light Resistance Testing Machine", Japanese Published Pat. No. 28956/1969, and U.S. Pat. No. 4,025,440.

However, for completely testing the light fastness/weather resistance by an accelerated test, the testing apparatus must maintain the temperature of the sample surface at a predetermined temperature, and must be able to direct light radiated from an artificial light source onto the sample and to simulate rainfall thereon, and to evaluate the extent of aging and deterioration of the sample by measuring changes in the sample over a period of time.

In such a light fastness/weather resistance testing machine, the most important point among the testing conditions is to hold the sample temperature uniform. To this end, it is necessary to simultaneously regulate both the air temperature in the testing tank and the black panel temperature so that they remain at a constant level irrespective of variations in the ambient temperature at the test site.

In the conventional machine as described above and in other similar machines, when the temperature of the sample surface is increased, the air flow regulator is operated to fully open the damper so that cool outside air is introduced to replace hot air in the tank, thereby cooling the interior of the tank. When the temperature in the tank is too low, the air flow regulator is operated to fully close the damper so that air from the tank is caused to recirculate thereinto.

In such a case, assuming that the air temperature regulator is preset to 40° C., for instance, the black panel thermometer 6 will display 63° C. This is for the condition that the ambient temperature ranges from 20° C. through 25° C.

However, whenever the ambient temperature varies outside the above-described range, the preset temperature must be modified accordingly. This is not only very inconvenient but often impossible in a continuous test over a long period of time, with the result that precise test results can not be obtained.

To eliminate the foregoing disadvantage, there has been used a means for using the black panel temperature regulator 7 to set the temperature of the black panel temperature regulator 7 to 63° C. in advance. However, this means has also created a problem as follows.

Because the temperature sensor of the black panel temperature regulator 7 which is a black stainless plate is relatively insensitive to variations in ambient temperature, it can not quickly detect such variations even if fresh air is introduced into the testing tank. As a result, the black panel temperature regulator 7 does not respond quickly, so that it gives an inaccurate reading, thereby making it impossible to indicate the precise temperature.

At the same time, the black panel thermometer 6 also suffers from a similar problem.

Further, when the ambient temperature is low, at the time of introduction of outside air, the sample is subjected to a sudden thermal stress because very cool air suddenly strikes the sample surface.

Consequently, the test results differ from those obtained by testing in open air at ambient temperatures.

Moreover, the very cool air strikes the sample surface beginning from its lower portion, which gives rise to another problem, namely the generation of a temperature difference between the upper and lower portions of the sample surface. Accordingly, this causes a difference in test results between the upper and lower portions of the sample, thereby preventing a precise evaluation of the characteristics of the sample.

When using a black panel temperature control system, for instance, assuming the ambient temperature to be 10° C. and a setting temperature of 63° C., the air temperature in the testing tank is about 40° C. As the air flow regulator is operated, air having a temperature 30° C. lower than the tank temperature strikes the sample surface, thereby causing thermal stress. Also, the temperature of the sample surface is lowered to 10° C. in the lower portion, 15° C. in the middle portion and 25° C. in the upper portion, so that precise test results can not be obtained.

Alternatively, when using the air flow regulator 8 only, even if the temperature regulator is set to hold the temperature of the sample surface constant, i.e., the temperature indicated by the black panel thermometer 6, the air temperature in the test tank can not be held constant for causing the black panel thermometer to display a constant temperature, because the temperature in the test tank varies largely depending on the ambient temperature of air introduced into the tank for temperature control.

When attempting to hold the black panel temperature constant at 63° C., for instance, the temperature in the test tank has to be set relatively high, i.e. at 43° C., for an outside air temperature of 5° C., but has to be set relatively low, i.e. at 38° C., for an outside air temperature of 30° C. It is in this way that the air temperature in the tank varies depending on the outside air temperature.

Further, the differences in temperature at the upper, middle and lower portions of the sample surface cause differences in the rate of deterioration of the sample among the upper, middle and lower portions thereof, thereby preventing precise evaluation of the test results.

Moreover, the Japanese Industrial Standard allows the black panel thermometer to be 63° C.±3° C. This is because, in the normal situations, the testing machine will not operate sufficiently accurately for an allowance of less than ±3° C.

Still further, as previously noted, the black panel thermometer is incapable of quickly responding to variations in tank temperature. This causes a lag between the temperature displayed by the thermometer and the actual temperature of the sample, so that precise test results can not be obtained.

To solve these problems, it has been proposed to install the testing machine in an environment of small temperature variation, for instance an air-conditioned space. However, this requires very expensive equipment.

As a practical matter, such a testing machine will normally be installed in a space which is not air-conditioned in many cases. Thus, the temperature in the installation site of the testing machine varies with the time of day and the season, as shown in FIGS. 7 and 8, respectively. In some regions, the difference in temperature between the summer and winter seasons is 45° C.

From the above, it can be seen that it is practically impossible to hold the temperature constant at all test sites as well as impossible to prevent variations in ambient temperatures.

OBJECT AND BRIEF SUMMARY OF THE INVENTION

The present invention has as an object the provision of a testing apparatus for solving the above-described problems, namely an apparatus for carrying out an accelerated light fastness/weather resistance test and which has an air mixing regulator which is capable of maintaining both the air temperature in the test tank and the black panel temperature constant irrespective of variations in the ambient temperature at the test site.

Another object of the present invention is to provide a light fastness/weather resistance test machine with an air mixing regulator which permits the test to be conducted at a uniform temperature without subjecting the sample surface to fluctuations in temperature irrespective of variations of the ambient temperature where the test machine is installed.

These objects are achieved by the provision of a light fastness/weather resistance accelerated test apparatus, comprising: a test tank having a discharge duct; a light source provided at the center of said test tank; a sample rotating frame in said test tank rotatable around said light source; a black panel thermometer mounted on said sample rotating frame; means on said sample rotating frame for sensing the temperature at the position of a sample on said sample rotating frame; an air flow regulator on said test tank and having an air intake; a blower mounted on said test tank for discharging air into the bottom of said tank; a circulating duct connected between said air flow regulator and said blower; a damper in said air flow regulator movable between a first position in which it opens said air intake to said circulating duct and opens the inside of said tank to said discharge duct and a second position in which it closes said air intake and said discharge duct and directs air from within said tank into said circulating duct; an air mixer having an intake connected to said air intake of said air flow regulator and a further damper in said intake, and further having a bypass opening therein between said further damper and said air flow regulator and between said discharge duct and said intake; a plurality of temperature sensors for detecting the air temperature outside said apparatus and a plurality of thermoregulators to which said temperature sensors are connected; and means connected to said further damper and to which said thermoregulators are connected for controlling the degree of opening of said further damper in response to the temperature outside said apparatus.

DETAILED DESCRIPTION OF THE INVENTION

Figure 2:
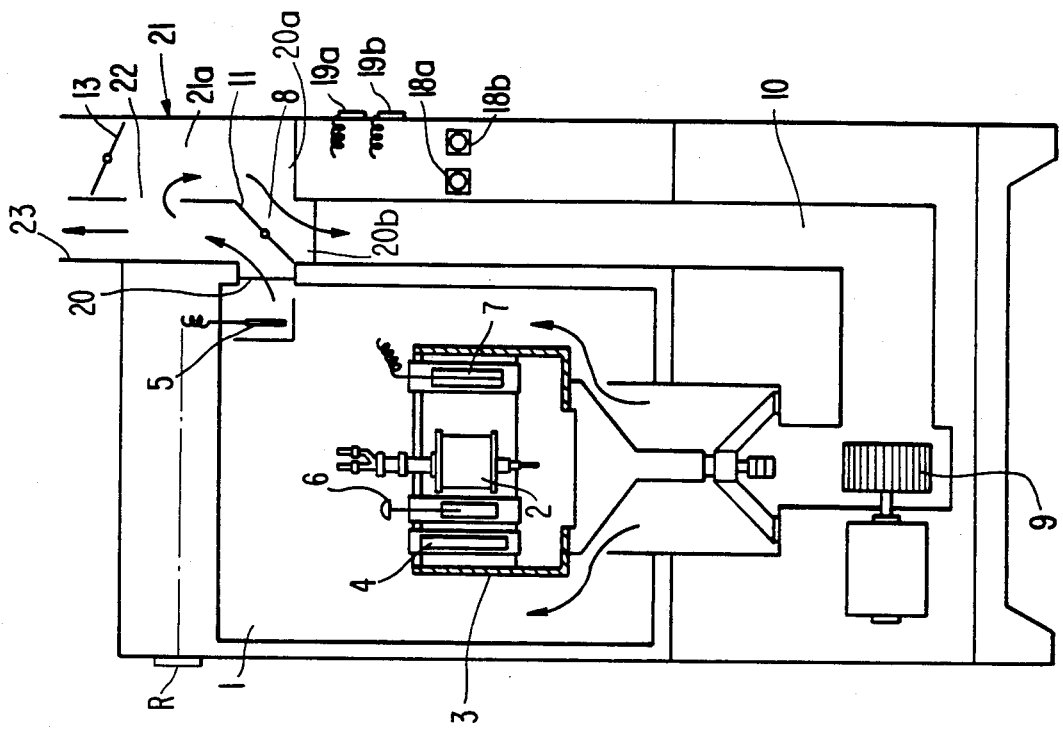
FIG. 2 is a sectional elevation view of a light fastness/weather resistance testing apparatus according to the invention.
Figure 1:
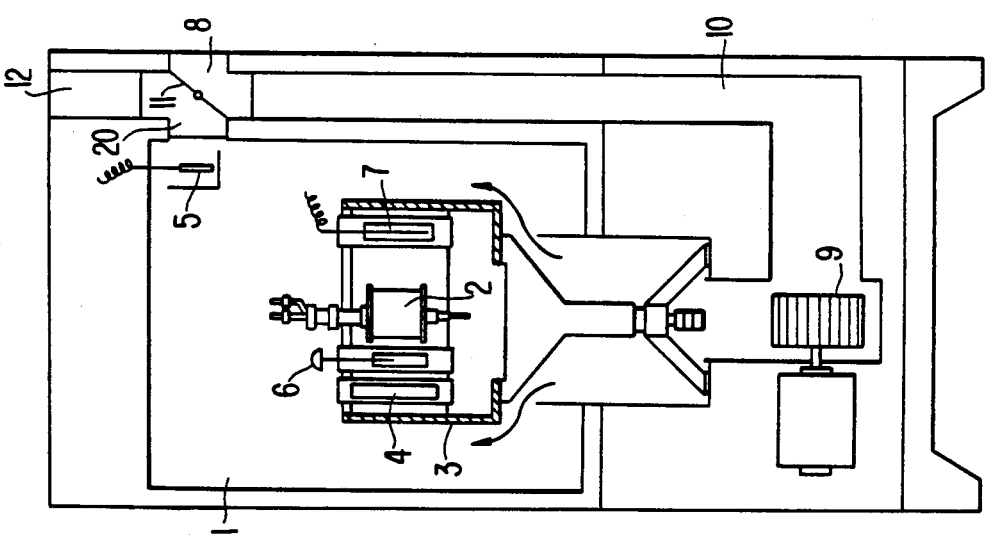
FIG. 1 is a sectional elevation front view of a prior art apparatus for carrying out accelerated light fastness/weather resistance tests.
Figure 4:
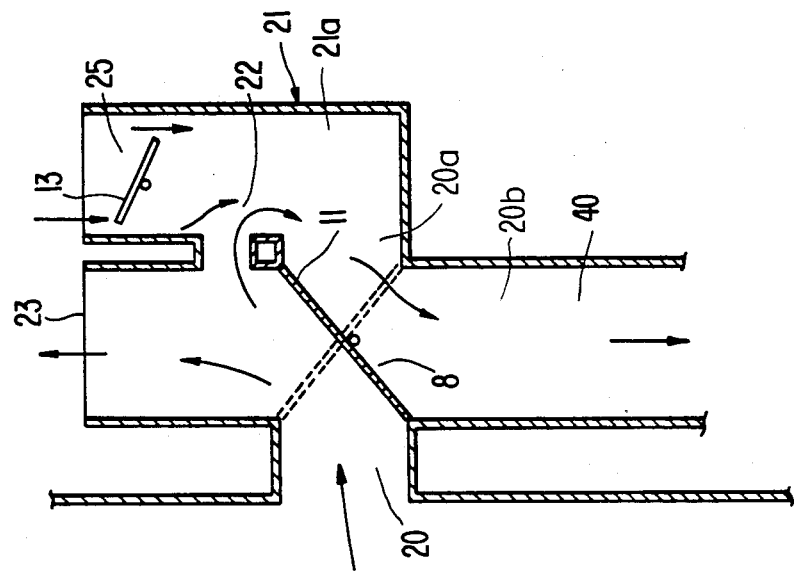
FIG. 4 is a sectional elevation view of part of the air mixing regulator of FIG. 3.
Figure 3:
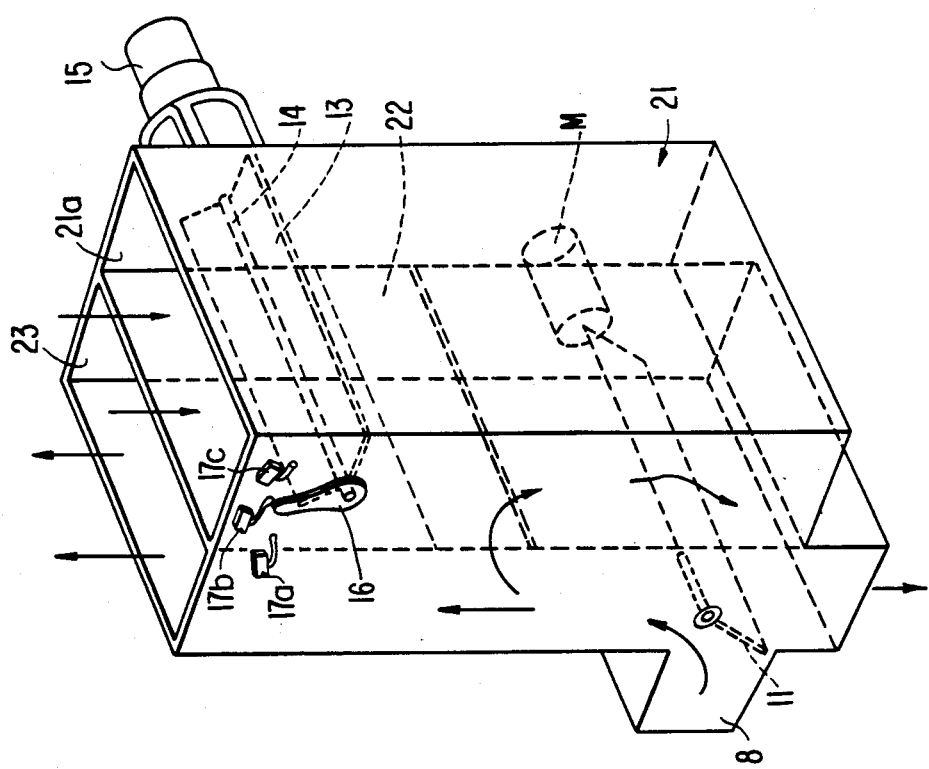
FIG. 3 is a perspective view of the air mixing regulator of the apparatus of the present invention.

As shown in FIGS. 2–4, the light fastness/weather resistance accelerated test machine according to the present invention comprises a black panel thermometer 6 mounted on a sample rotating frame 3 rotatable around a light source 2 provided at the center of a test tank 1. A conventional air temperature regulator R is mounted outside the test tank and has a temperature sensitive body 5 positioned in the test tank 1, adjacent the air flow exit 20 or a black panel temperature regulator 7 mounted on the sample rotating frame 3. An air flow regulator 8 is provided on the test tank 1 and has a recirculative air intake which is the air flow exit 20 and which opens to a tank discharge duct 23, an outside air intake 20a and a discharge 20b connected with a blower 9 provided on the testing machine base by a circulation duct 10. A first damper 11 is provided in the air flow regulator 8 between intakes 20 and 20a and which is caused to open and close in response to a signal from the air temperature regulator R or the black panel temperature regulator 7. An air mixer 21 is in communication with the air flow regulator 8 and comprises an intake duct 21a into which a bypass opening 22 opens from the tank discharge duct 23. The lower end of duct 21a opens into the air flow regulator 8. A plurality of temperature sensors 19a, 19b . . . are provided for detecting ambient temperature and a plurality of thermoregulators 18a, 18b . . . connected thereto are provided outside of the test tank 1.

A means is provided for adjusting the opening angle of a second damper 13 provided in the intake duct 21a upstream of bypass opening 22 in response to signals from the thermoregulators 18a, 18b . . . This means is constituted by a drive motor 15, a lever 16 and a plurality of limit switches 17 engageable by the lever 16 to disconnect power to the motor 15.

In operation, the air temperature in the tank is detected by the air temperature regulator R having the temperature sensitive body 5, or by the black panel temperature regulator 7 to open and close the damper 11 of the air flow regulator 8, so that the black panel temperature in the testing tank 1 is held constant. Opening and closing of the damper 11 is automatically controlled by making use of a known means (not shown) to actuate a drive motor M connected thereto.

For instance, when the temperature in the test tank 1 rises, the damper 11 of the air flow regulator 8 shifts from the position shown in dotted lines in FIG. 4 to the position indicated by solid lines therein, so that hot air in the tank is discharged through the tank discharge duct 23.

On the other hand, when the tank temperature falls to a predetermined temperature, the damper 11 is shifted to the position shown by dotted lines in FIG. 4 so that the air from the tank is now caused to recirculate thereinto.

When the damper 11 of the air regulator 8 is in the position shown by solid lines in FIG. 4, the air mixer 21 is designed to cooperate with the air flow regulator 8 so that changes in ambient temperature detected by the temperature sensors 19a, 19b cause the damper 13 of the air mixer 21 to be automatically operated by means of the drive motor 15 in response to signals from thermoregulators 18a, 18b, whereby the lever 16 provided at the end of the motor coupling shaft 14 is brought into engagement with one of the limit switches 17a, 17b, 17c to actuate the same, which disconnects the motor 15 thereby stopping the damper 13 at a predetermined position.

When the damper 11 of the air regulator 8 is in the position shown by solid lines in FIG. 4 to introduce outside air, it will be assumed that the thermoregulator 18a will be set at 10° C. and that the thermoregulator 18b to be set at 27° C., for instance. With an outside air temperature lower than 10° C., the lever 16 is stopped in the position of the limit switch 17a so that the degree of opening of the damper 13 is ¼ of the fully open position. With the outside air temperature in the range of 11° through 26° C., the lever 16 is stopped at the position of the limit switch 17b so that the degree of opening of the damper 13 is ½ of the fully open position, and with the outside air temperature higher than 27° C., the lever 16 is stopped at the position of the limit switch 17c so that the damper 12 is in a fully open state.

In this manner, the degree of opening of the damper 13 changes depending on variations in the ambient temperature so as to regulate a gap defined between the damper 13 and the inner wall of a duct 21a for the air mixer 21, thereby automatically controlling the amount of outside air drawn in through duct 21a depending on the ambient temperature.

Because the amount of air drawn in by the blower 9 is constant, the amount of hot air from the test tank 1 bypassed through bypass opening 22 between the discharge duct 23 and the air mixer 21 is also controlled in accordance with the extent of the gap defined between the damper 13 and the inner wall of the duct 21a. As a result, a controlled amount of hot air is introduced into the air mixer 21 to be mixed with fresh air to thereby provide air of a predetermined temperature, the thus mixed air coming into the test tank 1 through the circulation duct 10 and the blower 9. It rises up along the surface of the sample 4, and a part of it is discharged through the discharge duct 23 of the test tank and the air flow regulator 8 and the remainder is recirculated into the air mixer 21 again through opening 22.

When the tank temperature reaches a predetermined temperature, the damper 11 is shifted to the position shown by dotted lines in FIG. 4 in response to a signal transmitted from the black panel temperature regulator 7 or the air temperature regulator R, so that the air from within the test tank is caused to circulate through the circulation duct 10 and the blower 9. At the same time, introduction of fresh air is interrupted.

In the illustrated embodiment, there are provided two temperature sensors 19a, 19b and two thermoregulators 18a, 18b corresponding thereto as means for controlling the opening and closing of the damper 13, and there are further provided three limit switches 17a, 17b, 17c.

The opening and closing means in the present invention is not limited to the above embodiment, and by increasing the number of temperature sensors 19, thermoregulators 18 and limit switches 17, it becomes possible to regulate the opening angle of the damper 13 in an appropriate manner so that mixed air with a more closely controlled temperature can be fed into the test tank 1 depending on variations in the outside air temperature.

Figure 6:
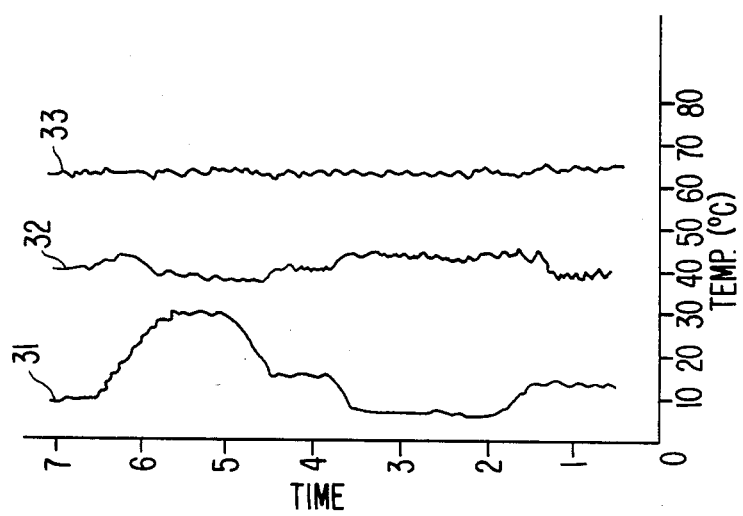
FIGS. 5 and 6 are graphs showing results of experiments using the test apparatus of the present invention as compared with the prior art apparatus.
Figure 5:
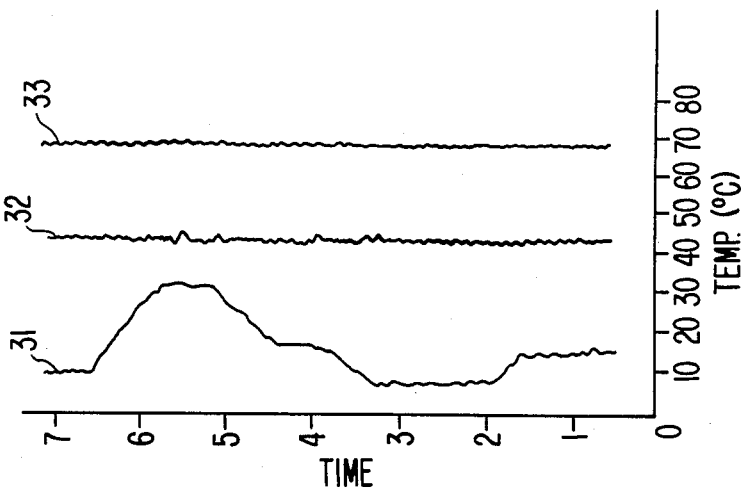

FIGS. 5 and 6 show experimental results obtained by using the test machine of the present invention and a conventional one, respectively, in the form of graphs in which the ordinate represents elapsed time and the abscissa represents temperature. In these graphs, curve 31 is the outside air temperature, curve 32 is the temperature in the test tank and curve 33 is the black panel temperature.

Both the experiments were conducted with the black panel temperature preset at 63° C. With the present invention, as will be seen from FIG. 5, the temperature in the test tank is held constant at all times even with variations in the open-air temperature. Conversely, in the case of the prior art apparatus, as shown in FIG. 6, it is seen that the temperature in the test tank changes with variations in the outside air temperature.

As will be apparent from the above experiments, the present invention is capable of holding the temperature in the test tank constant despite variations in the ambient temperature, whereby stable conditions can be maintained and effective test results can be reliably obtained.

Figure 7:
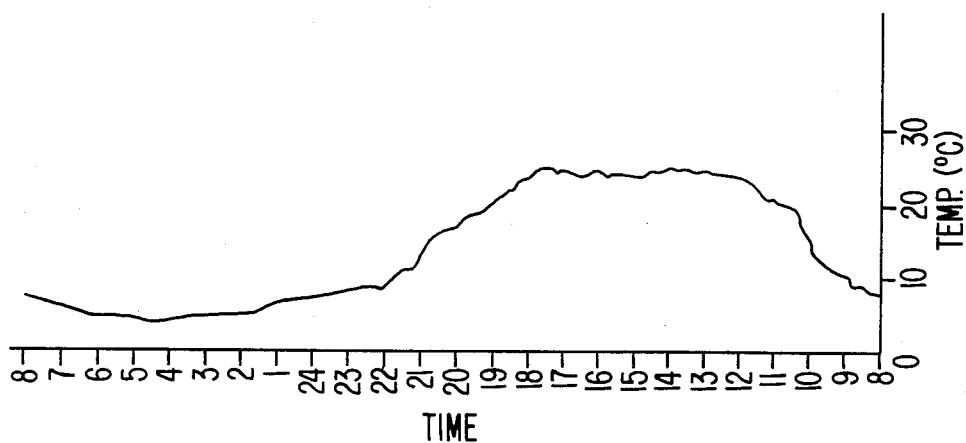
FIG. 7 is a graph showing daily changes in temperature in the test apparatus.
Figure 8:
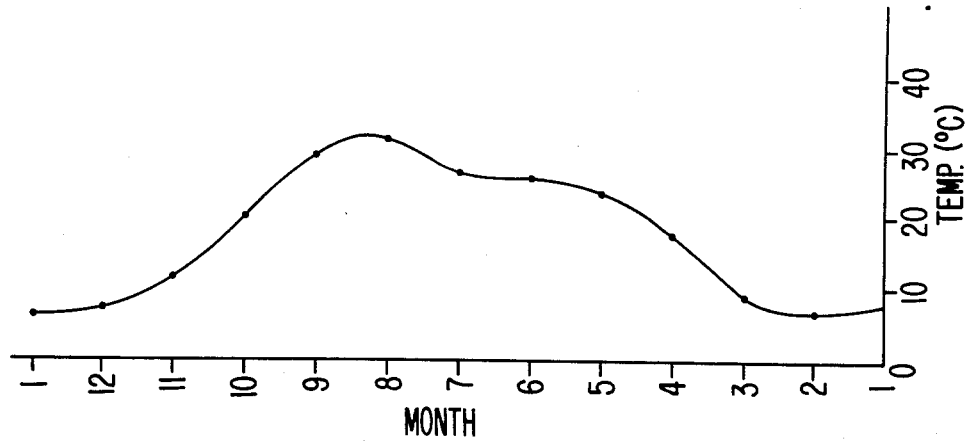
FIG. 8 is a graph showing annual changes in temperature in the test apparatus.

FIGS. 7 and 8 are graphs showing the temperature within the tank of the apparatus of the present invention, FIG. 7 being over a course of a month (with days 25-31 being omitted) and FIG. 8 being over twelve months.

Figure 9:
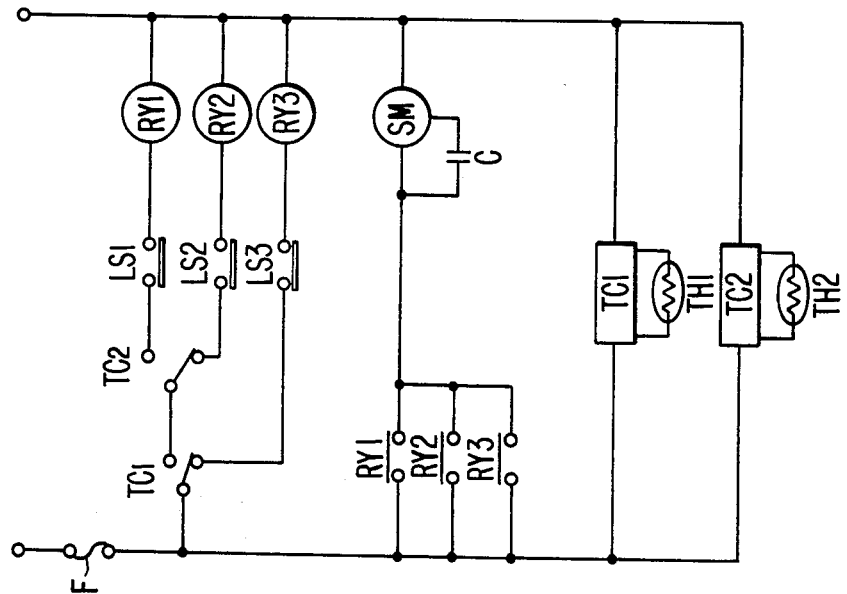
FIG. 9 is a circuit diagram of means for opening and closing the damper of the apparatus of the present invention.

FIG. 9 shows an electrical circuit diagram of the means for opening and closing the damper 13. In this figure, TC1 and TC2 are thermoregulators corresponding to 18a and 18b; TC$_1$ and TC$_2$ are contacts for the thermoregulators; TH1 and TH2 are temperature sensors; F is a fuse; LS1, LS2 and LS3 are limit switches corresponding to switches 17a, 17b and 17c; RY1, RY2 and RY3 are relays; SM is a motor corresponding to motor 15 and C is a capacitor.

EFFECT OF THE INVENTION

With the present invention constructed as described above, it is possible to avoid changes in the test tank temperature due to variations in the ambient temperature thereby maintaining a constant test tank temperature, despite a wide range of temperatures (e.g., 5° through 30° C.) at a testing site.

It is therefore possible to eliminate the differences in accelerated aging results among the upper, middle and lower portions of the sample, thereby insuring reproducible, accurate test results.

Furthermore, the present invention enables constant regulation of both the air temperature in the test tank and the black panel temperature irrespective of variations in the ambient temperature at the testing site.

Moreover, the present invention permits the test to be conducted at a stable, predetermined temperature without subjecting the sample surface to fluctuations in the temperature, irrespective of variations in the ambient temperature at the testing site.

What is claimed is:

1. A light fastness/weather resistance accelerated test apparatus, comprising:
  a test tank;
  a light source provided at the center of said test tank;
  a sample rotating frame in said test tank rotatable around said light source;
  a black panel thermometer mounted on said sample rotating frame for sensing the temperature in said test tank at the position of a sample on said sample rotating frame;
  an air flow regulator on said test tank and having a recirculation air intake opening therewith from said test tank and a tank discharge duct to which said recirculation air intake opens, an outside air intake and a discharge;
  a blower mounted on said test tank for discharging air into the bottom of said tank;
  a circulating duct connected between the discharge of said air flow regulator and said blower;
  a first damper in said air flow regulator movable between a first position in which it opens said outside air intake to said discharge and opens the recirculation air intake to said tank discharge duct, and a second position in which it closes off said outside air intake and said tank discharge duct from said discharge and said recirculation air intake and directs air from said recirculation air intake into said discharge;
  an air mixer having an intake duct with one end connected to said outside air intake of said air flow regulator and a second damper in said intake duct, and further having a bypass extending from said tank discharge duct and openng into said intake duct between said second damper and said outside air intake of said air flow regulator;
  test tank air temperature regulating means having temperature sensing means in said test tank and connected to said first damper for controlling said first damper to move in response to the test tank air temperature;
  a plurality of temperature sensors for detecting the air temperature outside said apparatus in the vicinity of the apparatus and a plurality of thermoregulators to which said temperature sensors are connected; and
  means connected to said second damper and to which said thermoregulators are connected for controlling the degree of opening of said second damper in response to the temperature outside said apparatus.

2. An apparatus as claimed in claim 1 in which said regulating means comprises an air temperature regulator outside said tank and having a temperature sensor in said test tank adjacent said recirculation air intake.

3. An apparatus as claimed in claim 1 in which said regulating means comprises a black panel temperature regulator including temperature sensing means and mounted on said sample rotating frame.

4. An apparatus as claimed in claim 1 in which said means for controlling the degree of opening of said second damper comprises a driving motor connected to said second damper, a lever mounted on said second damper, and a plurality of limit switches mounted in the path of movement of said lever as said second damper is rotated, said limit switches being connected to said drive motor for causing said drive motor to stop rotation when said second damper reaches a predetermined rotational position.

5. An apparatus as claimed in claim 4 in which said thermoregulators are connected to said limit switches and said drive motor for controlling opertaion of said drive motor.

6. An apparatus as claimed in claim 5 in which there are two temperature sensors, two thermoregulators, and three limit switches.

* * * * *